United States Patent [19]
Masaki et al.

[11] Patent Number: 5,576,341
[45] Date of Patent: Nov. 19, 1996

[54] 2-[[2-(N-ISOBUTYL-N-METHYL)AMINO]BENZYLSULFINYL]-BENZIMIDAZOLE AS ANTIMICROBIAL AGENT

[75] Inventors: Mitsuo Masaki; Tomio Yamakawa; Yutaka Nomura, all of Chiba; Hitoshi Matsukura, Saitama, all of Japan

[73] Assignee: Nippon Chemiphar Co., Ltd., Tokyo, Japan

[21] Appl. No.: 228,750

[22] Filed: Apr. 18, 1994

[30] Foreign Application Priority Data

Apr. 16, 1993 [JP] Japan .................................. 5-113942

[51] Int. Cl.⁶ .................................................. A61K 31/415
[52] U.S. Cl. .................................................. 514/395
[58] Field of Search .................................. 514/395

[56] References Cited

U.S. PATENT DOCUMENTS

| | | | |
|---|---|---|---|
| 5,013,743 | 5/1991 | Iwahi et al. | 514/338 |
| 5,196,205 | 3/1993 | Borody | 514/398 |

FOREIGN PATENT DOCUMENTS 2163747  8/1992  United Kingdom .

*Primary Examiner*—Jerome D. Goldberg
*Attorney, Agent, or Firm*—McAulay Fisher Nissen Goldberg & Kiel, LLP

[57] ABSTRACT

2-[[2-(N-Isobutyl-N-methyl)amino]benzylsulfinyl]benzimidazole is effective for treating or preventing Helicobacter infections by administration to patients suffering from the infection.

2 Claims, No Drawings

2-[[2-(N-ISOBUTYL-N-METHYL)AMINO]BENZYLSULFINYL]-BENZIMIDAZOLE AS ANTIMICROBIAL AGENT

BACKGROUND OF THE INVENTION

1. Field of Invention

The present invention relates to a novel antimicrobial agent which is effective to inactivate *Helicobacter pylori* (which is formerly named *Campylobacter pylori*) and therefore is effective to treat or prevent infections caused by *Helicobacter pylori*.

2. Description of Prior Art

U.S. Pat. No. 5,013,743 (corresponding to Japanese Patent Provisional Publication No. 3-173817) discloses that pyridine derivatives having a specific formula such as 2-(2-pyridyl)methylsulfinylbenzimidazole are effective to inactivate *Campylobacter pylori*.

ANTIMICROBIAL AGENTS AND CHEMOTHERAPY, March 1991, p.490–496 describes that lansoprazole and omeprazole have antimicrobial activity against *Helicobacter pylori*.

Japanese Patent Provisional Publication No. 3-161440 (published on Jul. 11, 1991) discloses that condensed imidazole derivatives having a benzopyran, benzothiopyran, tetrahydroquinoline, or indoline ring are effective to inactivate *Campylobacter pylori*.

U.S. Pat. No. 5,093,342 discloses that 5-methoxy-2[[(4-methoxy-3,5-dimethyl-2-pyridinyl)methyl]sulfinyl]-1H-benzimidazole is effective for treating infectious diseases caused by *Campylobacter pylori*.

WO89/03219 (published on Apr. 20, 1989, which corresponds to U.S. Pat. No. 5,196,205) discloses that a bismuth compound is effective to treat infections caused by *Campylobacter pylori*.

Further, a number of studies concerning relationship between *Helicobacter pylori* and peptic ulcer or gastritis have been reported. For instance, "Advance of Medical Science (in Japanese)", Vol. 159, No. 10, 1991, pp. 795 is mentioned. There is a report suggesting a relationship between *Helicobacter pylori* and recurrence of duodenal ulcer.

U.K. published patent application No.2163747 discloses a condensed imidazole derivative which is effective as an anti-ulcer agent, but is silent with respect to antimicrobacterial activity against to *Helicobacter pylori*.

SUMMARY OF THE INVENTION

An object of the present invention is to provide a new antimicrobial agent against to *Helicobacter pylori*.

The invention provides a method for treating or preventing infections caused by *Helicobacter pylori* comprising administering to a patient suffering therefrom 2-[[2-(N-isobutyl-N-methyl)amino]benzylsulfinyl]benzimidazole in an amount sufficient to the treatment or prevention of the infection.

The invention also provides a method for inactivating *Helicobacter pylori* comprising bringing 2-[[2-(N-isobutyl-N-methyl)amino]benzylsulfinyl]benzimidazole into contact with *Helicobacter pylori*.

DETAILED DESCRIPTION OF THE INVENTION

The 2-[[2-(N-isobutyl-N-methyl)amino]benzylsulfinyl] benzimidazole is described in the aforementioned U.K. published patent application No.2163747, and per se is known. This compound can be used in the form of a pharmaceutically acceptable salt such as sodium or potassium salt.

The antimicrobacterial activity of the instant compound against *Helicobacter pylori* is shown by the following experimental data.

EXPERIMENTAL 1

(1) Test compound: 2-[[2-(N-isobutyl-N-methyl)amino] benzylsulfinyl]benzimidazole dissolved in dimethylsulfoxide (DMSO) to give a solution of 80,000 µg/mL, and diluted by two-step dilution (2) MIC measurement: MIC(minimal inhibitory concentration) was determined by the following agar plate dilution method defined by Chemotherapy Society of Japan (Chemotherapy, vol. 29, 76–77(1991):

The solution of test compound (100 µL) was placed on a glass plate (diameter: 9 cm). Into the solution was placed 9.9 mL of Brucella Broth (BBL) containing 10% of horse lysed blood, to give a plate agar medium for the measurement. The bacterial suspension of *Helicobacter pylori* was adjusted to have turbidity equivalent to McFarland standard 0.5 ($10^8$ cfu/mL) and it was diluted with a sterile saline to give a bacterial suspension of $10^7$ cfu/mL. The bacterial suspension was inoculated on the plate agar medium containing the test compound using a microplanter. The medium was incubated at 35° C. for 6 days in 15% carbon dioxide gas. The MIC (µg/mL) was determined by amount of growth.

It was observed that MIC of the test compound (2-[[2-(N-isobutyl-N-methyl)amino]benzylsulfinyl]benzimidazole) showed MIC of 12.5 µg/mL. Accordingly, antimicrobial activity of the compound against *Helicobacter pylori* was confirmed.

EXPERIMENTAL 2

(1) Test strain: juvenile strains of Standard strains (ATCC 43526, ATCC 43579, ATCC 43629, and NCTC 11637), two subcultured strains (Wild 1 & Wild 2).

(2) Test compound: (1) 2-[[2-(N-isobutyl-N-methyl) amino]benzylsulfinyl]benzimidazole dissolved and diluted as in Experimental 1

(2) Omeprazole prepared in Laboratories of Nippon Chemiphar Co., Ltd., which was dissolved and diluted as in Experimental 1

(3) Cimetidine purchased from Sigma Corporation, which was dissolved and diluted as in Experimental 1

(4) Famotidine purchased from Sigma Corporation, which was dissolved and diluted as in Experimental 1

(3) MIC measurement: the same manner as in Experimental 1

The results of the observation are shown in Table 1.

TABLE 1

| Strain | MIC (µg/mL) | | | |
|---|---|---|---|---|
| | Compound (1) | Omeprazole | Cimetidine | Famotidine |
| ATCC 43526 | 25 | 12.5 | 800 | >800 |
| ATCC 43579 | 25 | 12.5 | 800 | 800 |
| ATCC 43629 | 12.5 | 12.5 | 800 | 800 |
| NCTC | 25 | 50 | — | — |

TABLE 1-continued

| Strain | MIC (µg/mL) | | | |
|---|---|---|---|---|
|  | Compound (1) | Omeprazole | Cimetidine | Famotidine |
| 11637 Wild 1 | 50 | 50 | — | — |
| Wild 1 | 50 | 50 | — | — |

In Table 1, "-" means that no test was done.

As is apparent from the data set forth in Table 1, 2-[[2-(N-isobutyl-N-methyl)amino]benzylsulfinyl]benzimidazole of the invention shows antimicrobial activity of MIC in the range of 12.5–50 µg/mL against the standard strains as well as wild strains, which is comparable to Omeprazole, that is, the known antimicrobial agent for *Helicobacter pylori*, while Cimetidine and Famotidine, that is, known $H_2$-blocker, show low antimicrobial activity to *Helicobacter pylori*.

The [[2-(N-isobutyl-N-methyl)amino]benzylsulfinyl] benzimidazole of the invention and its pharmaceutically acceptable salt can be administered orally to patients to treat or prevent infectious diseases caused by *Helicobacter pylori*. The dose may usually be about 0.1 mg/kg/day to 200 mg/kg/day. The adiministration can be done once or more a day. The dose may be either increased or decreased depending on the age, body weight, and other conditions of the patients.

A variety of preparation forms can be adopted. For instance, tablets, powder, granules, capsules, troche, syrup, emulsion, soft gelatin capsules, cream, gel, paste, and spray can be utilized. For these preparations, carriers, excipients, and other known additives can be employed. As the carriers, solid carriers such as lactose, kaolin, sucrose, crystalline cellulose, starch, talc, agar, pectin, magnesium stearate, and lecithin can be mentioned. Also employable are liquid carriers such as glycerol, polyvinyl pyrrolidone, olive oil, ethanol, benzyl alcohol, propylene glycol and water.

The compound of the invention can be also adminstered in combination with other antimicrobial agents such as antibiotics.

The preparation examples are given below. The active compound means [[2-(N-isobutyl-N-methyl)amino]benzylsulfinyl]benzimidazole of the invention.

PREPARATION EXAMPLE 1

[Capsules]

The below-mentioned composition was mixed and charged into a hard gelatin capsule to give a capsulated agent.

| (1) Active compound | 40 mg/capsule |
|---|---|
| (2) Lactose | 200 |
| (3) Starch | 50 |
| (4) Polyvinylpyrrolidone | 2 |
| (5) Crystalline cellulose | 35 |
|  | Total 350 mg/capsule |

PREPARATION EXAMPLE 2

[Tablets]

The below-mentioned composition was granulated in an aqueous povidone solution, and to the granuates was added magnesium stearate and pressed to give a tablet.

| (1) Active compound | 50 mg/tablet |
|---|---|
| (2) Lactose | 103 |
| (3) Starch | 50 |
| (4) Magnesium stearate | 2 |
| (5) Hydroxypropylcellulose | 15 |
|  | Total 220 mg/tablet |

What is claimed is:

1. A method for treating infections caused by *Helicobacter pylori* consisting essentially of administering to a patient 2-[[2-(N-isobutyl-N-methyl)amino]benzylsulfinyl]benzimidazole in an amount sufficient to the treatment of the infection.

2. A method for inactivating *Helicobacter pylori* consisting essentially of bringing 2-[[2-(N-isobutyl-N-methyl)amino]benzylsulfinyl]benzimidazole into contact with *Helicobacter pylori* in a patient.

* * * * *